United States Patent
Kreuz et al.

(10) Patent No.: US 9,795,409 B2
(45) Date of Patent: Oct. 24, 2017

(54) TROCAR DEVICE AND USE THEREOF

(71) Applicant: TrokaSure GmbH & Co. KG, Wittichenau (DE)

(72) Inventors: Gerold Kreuz, Wittichenau (DE); Heinrich Koch, Traunrreut-Matzing (DE)

(73) Assignee: TROKASURE GBR, Wittichenau (DE)

( * ) Notice: Subject to any disclaimer, the term of this patent is extended or adjusted under 35 U.S.C. 154(b) by 101 days.

(21) Appl. No.: 14/443,864

(22) PCT Filed: Nov. 18, 2013

(86) PCT No.: PCT/EP2013/074063
§ 371 (c)(1),
(2) Date: May 19, 2015

(87) PCT Pub. No.: WO2014/079807
PCT Pub. Date: May 30, 2014

(65) Prior Publication Data
US 2015/0297260 A1    Oct. 22, 2015

(30) Foreign Application Priority Data
Nov. 20, 2012 (DE) .................. 10 2012 111 192

(51) Int. Cl.
*A61B 17/34* (2006.01)
*A61B 17/00* (2006.01)

(52) U.S. Cl.
CPC .......... *A61B 17/3496* (2013.01); *A61B 17/34* (2013.01); *A61B 17/3421* (2013.01);
(Continued)

(58) Field of Classification Search
CPC ............ A61B 2017/3484; A61B 17/34; A61B 17/3421; A61B 17/3417; A61B 2017/00986; A61B 2017/3454; A61B 2017/346; A61B 2017/347; A61B 2017/3492; A61M 25/04; A61M 2039/0626
(Continued)

(56) References Cited

U.S. PATENT DOCUMENTS 3,490,457 A * 1/1970 Petersen ............... A61M 25/04
                                                    604/105
3,713,447 A    1/1973 Adair
(Continued)

FOREIGN PATENT DOCUMENTS

DE    69026883 T2    10/1996
DE    69211944 T2    12/1996
(Continued)

OTHER PUBLICATIONS

International Search Report and Written Opinion issued in PCT/US2013/074063, dated Mar. 13, 2014.

*Primary Examiner* — Katherine M Shi
(74) *Attorney, Agent, or Firm* — Heslin Rothenberg Farley & Mesiti P.C.

(57) ABSTRACT

The invention relates to a trocar sleeve or trocar and a trocar tip for minimally invasive/endoscopic surgical procedures carried out on people or animals. The trocar sleeve here has holding means in order to prevent the device from slipping out during the operation.

18 Claims, 3 Drawing Sheets

(52) U.S. Cl.
CPC ...... *A61B 17/3478* (2013.01); *A61B 17/3498* (2013.01); *A61B 17/3417* (2013.01); *A61B 2017/00867* (2013.01); *A61B 2017/00986* (2013.01); *A61B 2017/346* (2013.01); *A61B 2017/347* (2013.01); *A61B 2017/3454* (2013.01); *A61B 2017/3484* (2013.01); *A61B 2017/3488* (2013.01)

(58) Field of Classification Search
USPC .................................. 604/104, 105; 606/185
See application file for complete search history.

(56) References Cited

U.S. PATENT DOCUMENTS

| | | |
|---|---|---|
| 4,655,752 A | 4/1987 | Honkanen et al. |
| 4,943,280 A | 7/1990 | Lander |
| 4,978,341 A | 12/1990 | Niederhauser |
| 2003/0060770 A1 | 3/2003 | Wing et al. |
| 2005/0251190 A1 | 11/2005 | McFarlane |
| 2009/0306586 A1 | 12/2009 | Ross et al. |
| 2011/0144440 A1 | 6/2011 | Cropper et al. |
| 2011/0144447 A1 | 6/2011 | Schleitweiler et al. |
| 2011/0218565 A1 | 9/2011 | Criscuolo |
| 2012/0116303 A1* | 5/2012 | Marx ................. A61B 17/3415 604/98.01 |

FOREIGN PATENT DOCUMENTS

| | | |
|---|---|---|
| DE | 102008033375 A1 | 1/2010 |
| EP | 0567141 B1 | 9/1997 |
| EP | 1774918 A1 | 4/2007 |
| EP | 1015069 B1 | 12/2009 |
| JP | 2002-263061 A | 9/2002 |

* cited by examiner

TROCAR DEVICE AND USE THEREOF

CROSS REFERENCE TO RELATED APPLICATIONS

This application is a U.S. National Phase filing under 35 U.S.C. §371 of International Application No. PCT/EP2013/074063, filed Nov. 18, 2013, and published as WO 2014/079807-A2 on May 30, 2014, which claims benefit of priority from German Patent Application Serial No. DE 10 2012 111 192.8, filed Nov. 20, 2012. The entire contents of each of the prior applications are incorporated herein by reference in their entirety.

FIELD OF THE INVENTION

The invention relates to a trocar sleeve or trocar and also a trocar tip for minimally invasive/endoscopic surgical procedures carried out on humans and animals.

BACKGROUND OF THE INVENTION

The first laparoscopies were already published in 1944 by Hans Frangenheim and Raoul Palmer. However, Kurt Semm is considered to be the pioneer of the laparoscopic or pelviscopic operations, as his then spectacular procedures and inventions revolutionized surgery and, notwithstanding much hostility, became established in the preceding century by the middle of the seventies.

In the meantime, the overwhelming number of procedures in endoscopic and laparoscopic surgery is conducted minimally invasively. This affects all disciplines that involve active operations. The term "minimally invasive" or "keyhole surgery" designates operation techniques via the smallest access using instruments and cameras specially developed for this. Trocars are standard instruments in minimally invasive surgery whose use includes special features and risks.

The trocar is an instrument, sharp or blunt, with the aid of which during surgery an opening is created as an access to the body cavity following a previous skin incision. In general, the abdominal cavity is thereby previously inflated using pre-warmed CO2 in order to create better visual possibilities. This is held open using a trocar sleeve. This is generally a trocar pin, which, having an inner diameter of e.g. 3.0-12 mm, sits in the trocar sleeve, and whose point closes the opening in the trocar sleeve. The trocar is inserted e.g. through the abdominal wall or the navel into the abdominal cavity. The operator then has the possibility, following withdrawal of the trocar pin from the trocar sleeve, of looking through the trocar sleeve using optics (endoscope) or operating minimally invasively within the abdominal cavity using gripping, cutting or other instruments. (The diameters of the instruments are standardized so that trocars and instruments from various manufacturers fit together.) This can take place using a trocar head connected to the trocar sleeve, which has a gas-tight port for the previously listed instruments. Modern trocar systems are made either from surgical steel or medical plastic or a combination of these materials. They are offered as both reusable and disposable instruments. Taking into account the trend is increasingly towards disposable, as the preparation guidelines are becoming constantly more stringent, and trocars, due to their extant hollow spaces, are indexed as semi-critical instruments for reuse. The obturator or trocar pin is fitted to the trocar sleeve and can have a cutting as well as a blunt point. In addition, there are also so-called safety trocars, in which the cutting point is provided with a blade that withdraws after penetrating the abdominal wall in order to prevent injury to the internal organs. The trocar sleeves can have a valve mechanism or connection, which is used for suction, insufflation, etc. According to the prior art, trocar sleeves are available as rigid and flexible, in order to maintain the guiding characteristics for instruments during necessary manipulations with the instruments during the operation.

All minimally invasive procedures, primarily in the region of the abdominal cavity and pelvis, have in common the use of trocars for creating the access into the abdominal cavity and for inserting optics and instruments. Trocars and their daily use have become self-evident in the areas of gynecology, urology and surgery.

Trocar systems are known in the most varied of embodiments as both reusable and disposable systems. They consist in general of a trocar sleeve and a trocar pin moveable within the trocar sleeve, which pin is often equipped with a sharp cutting edge on its distal end for penetrating tissues.

Documents like US 2005/0251190 or US 2007/008827 describe gas-tight access paths using seals and connection systems. Sealing systems are also known from U.S. Pat. No. 4,943,280; U.S. Pat. No. 4,655,752; U.S. Pat. No. 4,978,341; EP 0 567 141, among others. The last named describes a valve system which enables the insertion of surgical instruments into the body of a patient, in particular via a trocar system. A gas-tight closure is guaranteed for instruments of various sizes.

More than 50% of complications take place intra-operatively and thus a fast handling on the part of the operator is necessary to avert life-threatening situations. It thereby occurs precisely in endoscopic operations, that in these extraordinary situations, instruments inserted via the trocar must be exchanged quickly and often. Very often, the trocars currently available on the market do not have the necessary holding function, e.g. in the abdominal wall, and slip out with the instruments. By this means, uncontrollable states can quickly arise, because a complex (time-consuming) new placement is necessary. This stress factor can lead to ongoing complications for the entire operating team. Thus, a trocar would be desirable which held securely in all situations, is atraumatic, has a favorable cost-benefit ratio, and last but not least can be placed and removed easily and without complications according to "surgical thinking."

Furthermore, trocar systems like the Kii Balloon Blunt Tip System (Applied Medical) are also known, which have an inflatable balloon in the front region of the trocar sleeve. After insertion of the trocar, air is thereby blown into the balloon, whereby this expands and should prevent the trocar from slipping out. The disadvantage in this system is primarily the arrangement of the balloon on the outside of the trocar, by which means the balloon must be guided along with the trocar through the insertion channel, which has proven to be a disadvantage in practical use. In addition, an additional connection has to be provided for the air supply, which generally hampers handling and increases the time for the operator to insert the trocar. Furthermore, the risk exists that the balloon undergoes damage during the operation due to its implementation, which can lead to a failing functionality of the balloon and the risk of the trocar slipping out during the operation.

DETAILED DESCRIPTION OF THE INVENTION

It is the underlying object of the current invention to provide an improved trocar sleeve and also an improved trocar pin for use on humans and animals.

This problem is solved by a trocar sleeve according to Claim 1, a trocar according to Claim 8, a trocar pin according to Claim 12 and a method according to Claim 18. Advantageous embodiments are indicated in the dependent claims.

A first aspect of the invention relates to a trocar sleeve which is designed in one piece, comprising a first and a second region, wherein the first region is designed for positioning within a body and has a holding means for preventing the trocar sleeve from slipping out of the body, wherein the holding means has areas designed like strips which are spaced apart from each other by openings in the trocar sleeve. The strip-like regions thereby have a curved original state so that the strip-like regions have a mushroomed state. The strip-like regions are thereby designed in such a way that these can transition from a curved original state into an extended state. In the extended state, the strip-like regions are designed substantially planar and the surface of the trocar sleeve has a substantially closed surface.

The inventive trocar sleeve additionally has a second region which is designed for accommodating a trocar pin.

A one-piece trocar sleeve is understood in the meaning of the invention to be designed from one workpiece. This can be manufactured, for example, using injection molding methods.

In one embodiment of the invention, the strip-like regions are formed from a shape memory material, or they are manufactured such that after the extension they return to their original state. Shape memory materials and/or manufacturing techniques are understood to be materials and/or manufacturing techniques which have or create a shape memory effect or can apparently "remember" their previous outer form despite an intermediate strong deformation. Shape memory materials or manufacturing techniques of this type are, for example, shape memory alloys and shape memory polymers and/or manufacturing techniques. The strip-like regions are thereby made from the shape memory material or the shape is formed such that these have a curved original state and thus effect a convergence of the first region of the trocar sleeve to the second region of the trocar sleeve. By this means, a mushrooming occurs in the strip-like region in the first region, by which means the trocar is prevented from slipping out of the body.

In one embodiment of the invention, the strip-like regions are made of shape memory material, wherein the shape memory material is a plastic.

In a further embodiment of the invention, the strip-like regions are designed as semicircular. The thus configured semicircular regions point the rounded side in the direction of the inner side of the trocar sleeve. In the direction of the outer side, the strip-like regions have a substantially smooth surface, which has a curve due to the cylindrically shaped configuration of the trocar sleeve. In the extended state, the strip-like regions are aligned flush with the first region. Due to the semicircular configuration of the strip-like regions, these are sufficiently stable in order to guarantee a repeated extension and flexion. Due to the substantially smooth surface, a risk of injury in the edge region of the insertion by, for example, ridges, hinges, or the like, is also prevented. During the extension, the semicircular inner side of the strip-like regions preferably fits into a recess formed on the trocar pin so that the strip-like regions and the recesses engage. The semicircular embodiment of the strip-like regions thereby guarantees in a simple way a simple and effortless manipulation of the trocar sleeve for the operator without thereby losing the guiding characteristics for the instruments to be inserted and without causing injuries to the tissues or peritoneum of the adjacent points.

In one embodiment of the invention, the second region is designed to be bend-proof.

In a further embodiment of the invention, at least the second region, preferably the entire trocar sleeve, has a substantially unvarying cross section in the extended state, which is designed to be circular, oval or round.

In a further embodiment of the invention, at least the second region, preferably the entire trocar sleeve, has a substantially unvarying cross section, which is designed to be circular. A circular cross section offers the advantage of stabilization during manipulation with instruments.

In a further embodiment of the invention, at least the second region, preferably the entire trocar sleeve, has a substantially unvarying cross section, which is designed to be oval. An oval cross section thereby enables more space for movement for the instruments, without needing to set tolerances that are too restrictive.

In a further embodiment of the invention, the trocar sleeve has outer markings for reading its inserted length. Using the markings applied to the exterior of the trocar sleeve, the inserted length of the trocar sleeve may be determined, by which means possible injuries to tissues or organs are avoided for the patients.

In a further embodiment of the invention, the trocar sleeve has a stop device. This stop device serves to prevent an autonomous slipping into the abdominal cavity or body cavity caused by manipulation with the instruments.

In a further embodiment of the invention, the trocar sleeve is designed to be bend-proof with exception of the strip-like regions.

In a further embodiment of the invention, the trocar sleeve has an inner diameter from 3-15 mm. Depending on the respective designated use, the trocar sleeve has, for example, an inner diameter from 3-3.5 mm, 5-5.5 mm or 7-7.5 mm or 10-10.5 mm or 12-12.5 mm.

In a further embodiment of the invention, the trocar sleeve has a wall thickness of 0.2-2 mm across at least a substantial part of the total length. Depending on the respective designated use, the trocar sleeve has a wall thickness from 0.5-1.0, or from 0.8-1.2, or from 1.0 or 1.5 mm.

In a further embodiment of the invention, the trocar sleeve has a working length of 70-230 mm. Depending on the respective designated use, the trocar sleeve has a total length of 70-80 mm or 80-90 mm or 110-120 mm, or 150-160 mm or 160-170 mm. The previously listed dimensions are particularly suited for the use via an access through the abdominal wall into the abdominal cavity or the pelvis.

In a further embodiment of the invention, the trocar sleeve has a front side in the first region, which is designed to have a different wall thickness.

In a further embodiment of the invention, the trocar sleeve has in the interior at least one means for the detachable arrangement of the trocar pin. The trocar pin is thereby inserted into the trocar sleeve and positioned in the trocar sleeve by means of the at least one positioning means. The positioning means may thereby be designed, for example, as means for a positive locking connection. For example, the positive locking connection may be carried out by means of a snap lock connection made from a latching groove and latching pin. The trocar sleeve may thereby have in the interior a locking groove or locking pin as a positioning means. It is also conceivable that multiple positioning means may be used for the positioning.

A further aspect of the invention relates to a trocar comprising a trocar sleeve according to the invention and also a trocar head.

In one embodiment of the invention, the trocar is implemented as one piece, whereby the trocar head is formed on a trocar sleeve according to the invention.

In one embodiment of the invention, the trocar is implemented as two pieces. The trocar sleeve and the trocar head are thereby connected to each other fluid- and gas-tight using an intermediate layer of a seal and/or a positive locking connection. The trocar head is thereby multiply reusable as a rule, whereby only the trocar sleeve is manufactured as a disposable product from a suitable material.

In one embodiment of the invention, the trocar is implemented as two parts, wherein the trocar sleeve and the trocar head are detachably connected to each other.

In one embodiment of the invention, a seal is detachably arranged inside of the trocar head.

In one embodiment of the invention, the trocar head comprises at least one gas-tight valve and/or at least one inlet and outlet for gases and/or liquids. The valve and/or the inlet and outlet are thereby used for insufflation with gas or for releasing of smoke arising from coagulation, which hampers vision.

A further aspect of the invention relates to a trocar pin with a first and a second region, wherein the second region is designed as tapered in comparison to the first region and wherein the first region has a front face. The front face may thereby taper to a conical point or be designed as blunt. To begin the operation, a trocar pin is used which has a tapering, conically pointed configuration, which is adapted in length and in diameter to the second region of the trocar sleeve in such a way that it substantially corresponds to the different side wall thickness of the first region of the trocar sleeve for better perforation of the abdominal wall. The first region of the trocar pin is shaped such that it provides the operator with the best possible load-saving and energy efficient method for piercing and insertion into the body cavity. According to the invention, the trocar pin has recesses which are designed to accommodate the strip-like regions of a trocar sleeve. The recesses are preferably arranged radially along the trocar pin, wherein the number of recesses corresponds to the number of the strip-like regions of the trocar sleeve. For example, 1 to 8, preferably 2 to 6, particularly preferably 2, 4 or 6 recesses are arranged along the trocar pin. The recesses preferably have a semicircular cross section.

In one embodiment of the invention, the trocar pin is implemented as one piece.

In a further embodiment, the trocar pin is designed as two parts, wherein the first and the second regions are detachably connected. By this means, the first region or the second region may be reused while the respective other region is configured as a disposable product. By this means, increased expenses caused by sterilization are avoided because only certain parts of the trocar pin must be made of a metal or alloy.

In a further embodiment of the invention, the front face of the trocar pin has a tapering, conical point or blunt, rounded configuration. The tapering, conically pointed front face thereby serves for the piercing by the trocar pin into the abdominal cavity. After ending the operation, the trocar must be removed again. This rounded, blunt trocar pin is used thereby for removing the trocar sleeve and prevents injuries (e.g. of the intestines) after the gas has been released from the abdominal cavity.

In a further embodiment of the invention, the trocar pin has at least one means for detachable positioning of the trocar pin in the trocar sleeve according to the invention. The trocar pin is thereby inserted into the trocar sleeve and positioned by means of at least one positioning means in the trocar sleeve. The positioning means may thereby be designed, for example, as means for positive locking connection. For example, the positive locking connection may be carried out by means of a snap lock connection made of a latching groove and latching pin. The trocar pin may thereby have a locking groove or locking pin as a positioning means. It is also conceivable that multiple positioning means may be used for the positioning.

A further aspect of the invention relates to a kit comprising a trocar sleeve according to the invention and also at least one trocar pin according to the invention. Advantageously, the kit comprises a trocar sleeve according to the invention and also a trocar point with a tapering, pointed conical front face and also a second trocar pin with a blunt, rounded front face.

A further aspect of the invention relates to a system comprising a trocar according to the invention and also at least one trocar pin according to the invention. Advantageously, the system comprises a trocar sleeve according to the invention and also a trocar point with a tapering, pointed conical front face and also a second trocar pin with a blunt, rounded front face.

A further aspect of the invention relates to the use of a kit according to the invention for endoscopic surgery and/or diagnosis.

A further aspect of the invention relates to the use of a system according to the invention for endoscopic surgery and/or diagnosis.

A further aspect of the invention relates to a method for tensioning the strip-like regions of a trocar sleeve according to the invention comprising the steps:

Insertion of a trocar pin into a trocar sleeve, wherein the trocar pin strikes on a front side in the interior of the trocar sleeve, Positioning of the trocar pin in the trocar sleeve by at least one detachable arrangement, whereby in the interior of the trocar sleeve, a positioning means for the detachable positioning engages with a positioning means of the trocar pin for detachable positioning, so that the trocar pin is moved in the distal direction, so that the strip-like regions are transitioned from a bent original state into an extended position by the distal movement of the trocar pin, by which means the trocar sleeve has a substantially closed surface, Removing the trocar pin from the trocar sleeve by detaching the arrangement, wherein the strip-like regions transition from an extended state into a curved original state.

In one embodiment of the invention, the detachable arrangement is carried out by a snap-in connection of a locking groove and a locking pin.

In one configuration of the embodiment, the snapping-in of the locking pin and locking groove takes place through a rotational movement of the trocar pin. During the rotation of the trocar pin, the locking pin and locking groove engage. The snap-in connection can be detached again by rotating the trocar pin in the opposite direction.

In one embodiment of the invention, the detachable arrangement is carried out by a positive locking connection. This can be designed, for example, as a clamp connection, a plug connection or a pin connection.

The mushrooming of the strip-like regions in the first region of the trocar sleeve prevents a complete or partial slipping out of the trocar sleeve during the operation. As a result of the mushrooming, the contact surface, which is formed by the mushroomed strip-like regions, is enlarged in such a way that this lies adjacent to the abdominal inner wall and safely prevents slipping out. The strip-like regions mushroomed in the "idle state" or "delivery state" are extended by the insertion and snap-in connection or rotation of the trocar pin and adapted to the outer diameter of the trocar sleeve. The dimensions are calculated such that no over extension and thus damage to the strip-like regions can occur. It is, however, quite conceivable that the system is already delivered in the "extended" state, whereby the trocar pin is arranged in the interior of the trocar sleeve.

Within the context of the use during surgical applications, there subsequently follows the removal of the trocar sleeve from the body, wherein the trocar pin is inserted again into the trocar sleeve and snapped in, by which means the strip-like regions are extended and a simple removal of the trocar sleeve is guaranteed.

Due to the repeated insertion and snapping-in or rotation of the trocar pin, there occurs an extension of the strip-like regions in the first region of the trocar sleeve, by which means the mushrooming is reversed and a simple removal of the trocar sleeve is now enabled.

The invention likewise relates to a method for preparing for a treatment, for the treatment or diagnosis in endoscopic surgery on people or animals. A method of this type comprises the provision of a trocar sleeve or a trocar, an obturator/trocar pin, and if necessary the corresponding operation thereof. The trocar pin according to the invention is inserted into the trocar sleeve according to the invention and if necessary rotated or positioned by means of a click mechanism, by which means a position of the trocar pin in the trocar sleeve occurs, by which means the mushroomed strip-like regions are extended. Afterwards, the insertion of the trocar in the operation region is carried out. Subsequently, the trocar pin is removed from the trocar sleeve, by which means the extension of the strip-like regions is released and these now mushroom in the interior of the body. After a successful operation, the trocar pin is inserted again and the strip-like regions are extended in turn. Afterwards, the trocar may be completely removed without great effort.

The present invention enables a safe, sterile access to the abdominal cavity. Further, it prevents the undesired slipping out of the trocar or the trocar sleeve due to insufficient autonomous holding functions in the abdominal wall, as could be determined by means of comparison tests. It was thereby determined that the seal(s) incorporated in the trocar head, which are supposed to guarantee the completely desired gas-tightness, offer a friction resistance to the inserted instruments which ensures a so-called carry-along effect, and which pulls the trocar sleeve either entirely or partially into the abdominal wall or pulls it completely out. A further advantage of the present invention is to specify a surgical instrument and method which enables a safe closure of the inlet opening after the completion of a surgical procedure.

The insertion takes place preferably through the abdominal wall up to the distal end of the trocar or the trocar sleeve remaining after the removal of the trocar pin, protruding somewhat beyond the peritoneum into the abdominal cavity, wherein the holding means, which are designed, for example, as a specially formed mushrooming, prevent on the one hand a slipping out of the insertion channel or a slipping in within the insertion channel. The specialized mushrooming is rigid, which means that after opening the mushrooming, a rigid state is achieved. Rigid additionally means that the trocar sleeve substantially retains its form and guide characteristics for instruments etc. during approved use. In addition, the holding means may, for example, be formed from a shape memory material.

Preferred refinements of the invention arise from the combinations of the claims or individual features thereof.

The invention shall be subsequently explained in more detail by means of a few embodiments and the associated figures. The embodiments shall thereby describe the invention without limiting it to these.

Figures 1, 2:
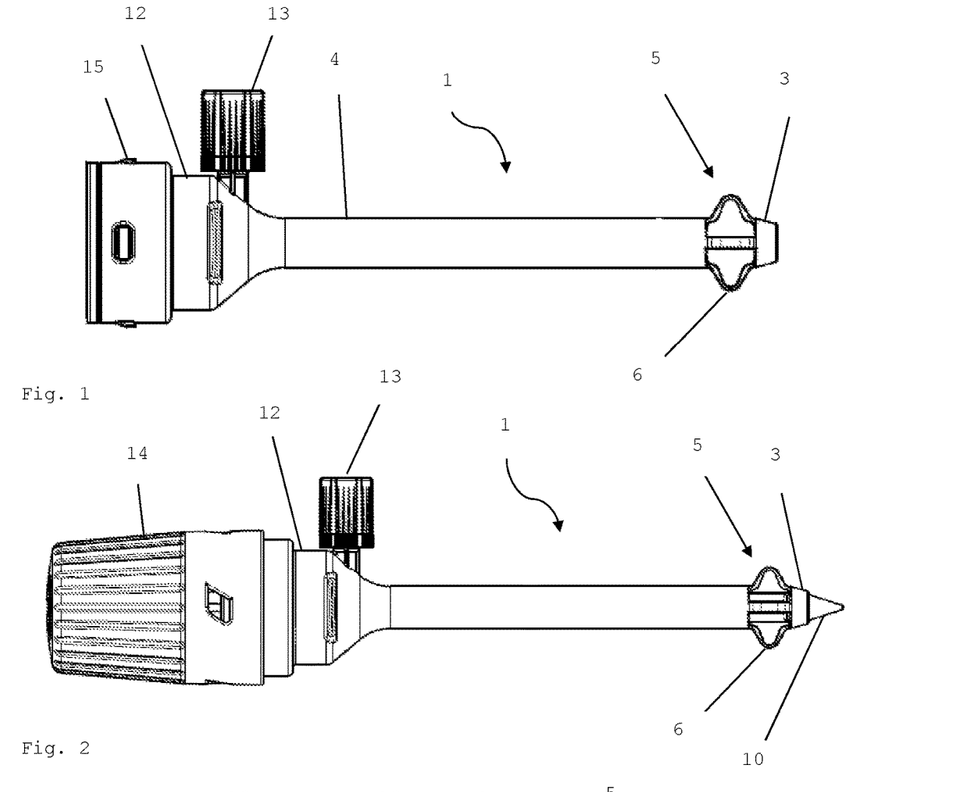
FIG. 1 shows a schematic cross sectional presentation of a trocar sleeve according to the invention with a mushrooming of the strip-like elements in the first region of the trocar sleeve.
FIG. 2 shows a schematic presentation of a trocar sleeve according to the invention with an inserted trocar pin according to the invention and a mushrooming of the strip-like elements in the first region of the trocar sleeve.

In a first embodiment, a trocar sleeve according to the invention is schematically presented in FIG. 1. The trocar sleeve 1 thereby has a first and a second region 3, 4. The first region 3 has, on its end, a front face which is conically implemented. The trocar sleeve has a holding means 5, which is designed for example as strip-like regions 6 in the first region 3. These strip-like regions may be formed thereby from a shape memory material, for example, a shape memory plastic, or using special manufacturing techniques and have, for example, a semicircular configuration in the direction of the interior of the trocar sleeve 1. The strip-like regions 6 are thereby in a curved position in the original state so that a mushrooming of the strip-like regions 6 is formed. The trocar sleeve 1 has additionally in FIG. 1 a trocar head 12, which comprises for example a gas-tight valve 13 and at least one latching pin 15.

A trocar sleeve 1 according to the invention with a trocar pin 2 according to the invention is represented in FIG. 2. It can be thereby recognized that the strip-like regions 6 are in a curved position, thus still in the original state.

A trocar pin 2 is arranged in the interior of the trocar sleeve 1, which likewise has a first and a second region 8, 9. The first region 8 is thereby designed to be a tapering, conical point and has a point 10, which is designed for piercing.

Figure 3:
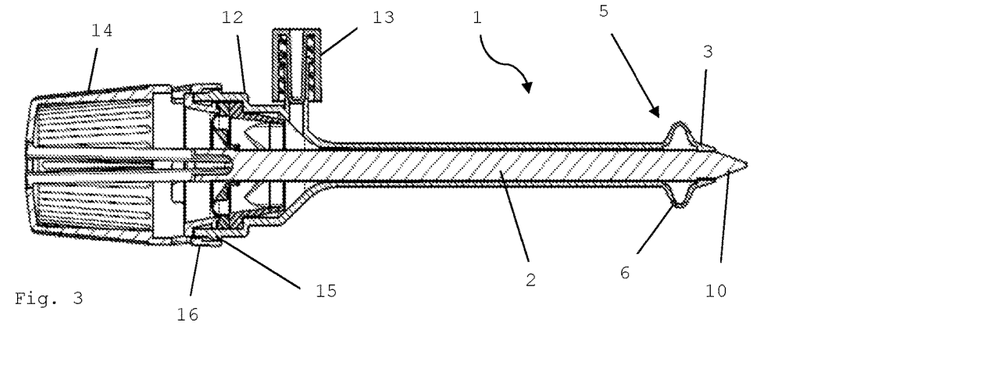
FIG. 3 shows a schematic cross sectional presentation of a trocar sleeve according to the invention with inserted trocar pin according to the invention and a mushrooming of the strip-like elements in the first region of the trocar sleeve.
Figure 4:
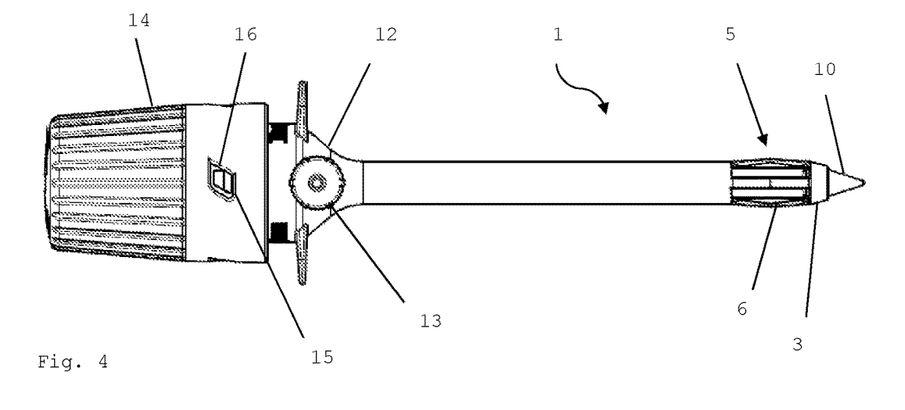
FIG. 4 shows a further schematic presentation of a trocar sleeve according to the invention with inserted trocar pin according to the invention and extended strip-like elements.

FIG. 3 shows a schematic cross sectional presentation of FIG. 2. The trocar pin 2 in the interior of the trocar sleeve 1 is thereby clearly recognizable. In addition, FIG. 3 shows that the locking pin 15, which is arranged on the trocar head 12, engages with a locking groove 16, which is arranged in the interior of the trocar pin handle 14. The locking pin 15 is engaged in the locking groove 16 by a snap-in locking, for example, by means of a rotational movement of the trocar pin handle 14, wherein the trocar pin 2 is moved in the direction of the first region 3 of the trocar sleeve 1. As a result, there is an extension of the strip-like regions 6, as this is depicted in FIG. 4. Due to the semicircular configuration of the strip-like regions 6, these may arrange themselves during extension into recesses 11 of the trocar pin 2 so that a substantially constant surface is formed. This is important in particular in the context of minimizing edge injuries. Due to the snap-in locking of locking pin 15 and locking groove 16, a constant extension of the strip-like regions 6 is guaranteed. In the extended state, the trocar is inserted in the operation area and subsequently the snap-in locking of locking pin 15 and locking groove 16 is released by rotating in the opposite direction, so that the trocar pin 2 may be removed from the trocar sleeve 1. The extension of the strip-like regions 6 is released by the release of the snap-in locking of locking pin 15 and locking groove 16. Due to the configuration of the strip-like regions 6 from a shape memory material, these again assume their original state, by which means a mushrooming occurs. Due to this mushrooming, which takes place in lumens, a slipping out of the trocar sleeve 1 is prevented.

To remove the trocar sleeve after completing the operation, the trocar pin 2, with round or blunt point as necessary, is inserted into the trocar sleeve 1 and a snap-in locking of the locking pin 15 and the locking groove 16 is effected in turn by rotation on the trocar pin handle 14. By this means, a repeated extension of the strip-like regions 6 occurs, by which means the mushrooming is released and the trocar sleeve 1 may be removed in turn.

Figure 5:
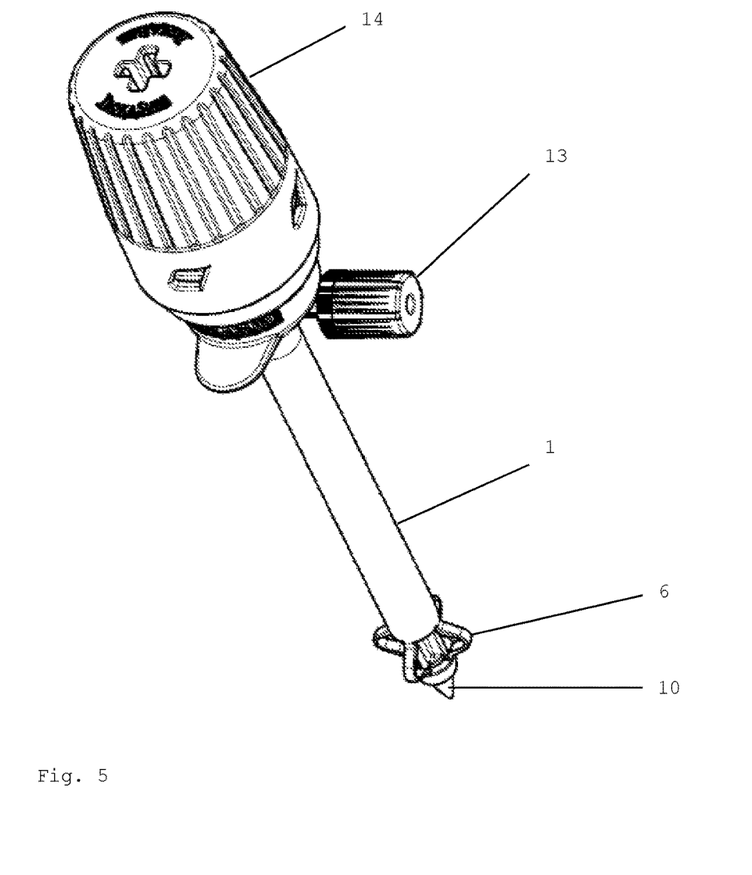
FIG. 5 shows a schematic presentation of a trocar sleeve according to the invention with inserted trocar pin according to the invention.

A trocar sleeve 1 with inserted trocar pin 2 is presented again in FIG. 5, wherein the strip-like regions 6 are clearly visible in the original state and are therefore mushroomed.

Figure 6:
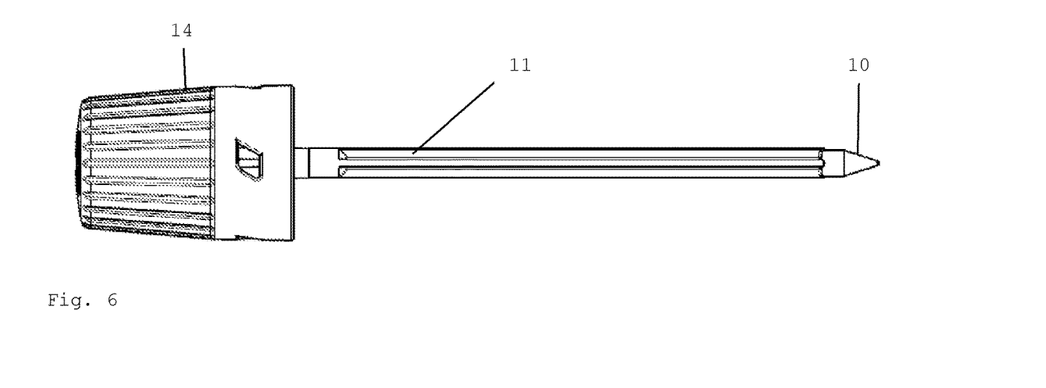
FIG. 6 shows a schematic representation of a trocar pin according to the invention.

A trocar pin 2 according to the invention is presented in FIG. 6, which has a first and a second region 8, 9. The trocar pin point 10 is designed as conically sharp in order to guarantee a simple piercing in the operation region. In addition, the trocar pin 2 according to the invention has recesses 11, which are arranged along the longitudinal axis of the trocar pin 2. These recesses 11 are thereby configured in order to accommodate the inner side of the strip-like regions 6, so that a substantially closed surface of the trocar sleeve 1 is formed.

In a further embodiment (not shown in more detail), the positioning of the trocar pin 2 in the trocar sleeve 1 is carried out by means of a clamping connection.

The application of the new invention is explained as an example of an intervention. The intra-abdominal lumen is easily accessible via the navel by means of a special Verres needle and the overblowing the abdomen with preheated $CO_2$ and also a special trocar, such as a camera trocar. Afterwards, the trocar sleeve according to the invention or trocars, so-called working trocars, are placed by sight. This may generally be 1-4 pieces according to the operation and execution; however, it is generally 2 pieces. The actual operation instrument(s) may be inserted via these. After the completion of the intra-abdominal procedure, the instrument(s) is/are removed and the cutaneous wound is closed as necessary.

LIST OF REFERENCES

1 Trocar sleeve
2 Trocar pin
3 First region of the trocar sleeve
4 Second region of the trocar sleeve
5 Holding means
6 Strip-like region
7 Front face of the first region of the trocar sleeve
8 Tapering, conically sharp first region of the trocar pin
9 Second region of the trocar pin
10 Point of the trocar pin
11 Recesses
12 Trocar head
13 Gas-tight valve
14 Trocar pin handle
15 Locking pin
16 Locking groove

What is claimed is:

1. A trocar kit comprising a one piece trocar sleeve and at least one removable trocar pin, wherein: the trocar sleeve includes a first and a second region, the first region is for positioning within a body and has a holding means for preventing the trocar sleeve from slipping out of the body, the holding means has strip-like elements circumferentially spaced at a distance from each other by openings in the trocar sleeve, the strip-like elements have a curved original state, resulting in a mushroomed state in the first region, the second region accommodates the at least one removable trocar pin, the at least one removable trocar pin comprises a first and a second region, the first region of the at least one removable trocar pin has a front face, and the at least one removable trocar pin has recesses to accommodate the strip-like elements of the trocar sleeve; and further comprising:
  a first element and a second element configured to engage each other in a detachable manner for detachable positioning of the at least one removable trocar pin in the trocar sleeve so that the strip-like elements having a curved original state are extended and adapted to an outer diameter of the trocar sleeve by insertion and connection or rotation of the at least one removable trocar pin within the trocar sleeve, and extension of the strip-like elements is released and the strip-like elements are returned to the curved original state by detaching the first and second elements from one another and removing the at least one removable trocar pin from the trocar sleeve.

2. The trocar kit according to claim 1, wherein the strip-like elements comprise a shape memory material.

3. The trocar kit according to claim 1, wherein the strip-like elements have semicircular shapes.

4. The trocar kit according to claim 1, wherein the trocar sleeve has outer markings for reading inserted length thereof.

5. The trocar kit according to claim 1, wherein the trocar sleeve has an inner diameter of 3-15 mm, a wall thickness of approximately 0.2-2 mm across at least a substantial portion of a total length of the trocar sleeve, and a total length of the trocar sleeve of 70-230 mm.

6. The trocar kit according to claim 1, wherein the trocar sleeve comprises the first element, and the first element has a locking pin for positioning the at least one trocar pin.

7. The trocar kit according to claim 6, wherein the at least one removable trocar pin comprises the second element and wherein the second element comprises a latching groove configured to engage with the locking pin of the trocar sleeve.

8. The trocar kit according to claim 1, further comprising a trocar head.

9. The trocar kit according to claim 8, wherein the trocar sleeve and trocar head together comprise one piece.

10. The trocar kit according to claim 8, wherein the trocar sleeve and trocar head comprise separate pieces detachably connected to each other.

11. The trocar kit according to claim 8, wherein the trocar head comprises at least one of: a gas-tight valve and at least one inlet or outlet for gases and/or liquids.

12. The trocar kit according to claim 1, wherein the at least one removable trocar pin comprises two pieces.

13. The trocar kit according to claim 1, wherein the at least one removable trocar pin has one of: a tapering, pointed, conical front face or a rounded, blunt, front face.

14. The trocar kit according to claim 1, adapted for endoscopic surgery and/or diagnosis.

15. A method for tensioning the strip-like elements of the trocar sleeve of the trocar kit according to claim 1, comprising the steps of:

inserting the at least one removable trocar pin into the trocar sleeve, wherein the front face of the at least one removable trocar pin strikes on a front side in an interior of the trocar sleeve, positioning of the at least one removable trocar pin in the trocar sleeve by the first and second elements, whereby in the interior of the trocar sleeve, a positioning means of the trocar sleeve engages with a positioning means of the at least one removable trocar pin for detachable positioning, so that the at least removable trocar pin is moved in a distal direction, the strip-like elements are transitioned from the curved original state into an extended position by the distal movement of the at least one removable trocar pin, and the trocar sleeve assumes a substantially closed surface, and removing the at least one removable trocar pin from the trocar sleeve by detaching the first and second elements from one another, wherein the strip-like elements transition from the extended state into the curved original state.

16. The method according to claim 15, wherein the detachable positioning is carried out using a positive locking connection.

17. The method according to claim 15, wherein the detachable positioning is carried out by snap-in locking of the at least one removable trocar pin and the trocar sleeve by a snap-in mechanism.

18. The method according to claim 17, wherein the snap-in locking is carried out by the first element which comprises a locking pin and the second element which comprises a locking groove by rotating the at least one removable trocar pin in the trocar sleeve.

* * * * *